US012731660B2

(12) United States Patent
Pieringer Baeza et al.

(10) Patent No.: US 12,731,660 B2
(45) Date of Patent: Sep. 8, 2026

(54) METHODS AND SYSTEMS FOR DESIGNING PHAGE COCKTAILS

(71) Applicant: PHAGELAB CHILE SPA, Santiago (CL)

(72) Inventors: Christian Philip Pieringer Baeza, Santiago (CL); Felipe Alberto Rojas Aracena, Santiago (CL); Antonio Andres Ossa Guerra, Santiago (CL); Nicolas Cifuentes Munoz, Santiago (CL); Matias Aguilera Barrios, Santiago (CL); Rodrigo Norambuena Venegas, Santiago (CL); Eduardo Tobar Calfucoy, Santiago (CL); Andrea Veronica Sabag Matilla, Santiago (CL); Onix Andriet Cifuentes Figueroa, Santiago (CL); Pablo Cifuentes Palma, Santiago (CL); Hans Pieringer Castro, Santiago (CL); Nicolas Alexis Berman, Buenos Aires (AR)

(73) Assignee: PHAGELAB CHILE SPA, Santiago (CL)

( * ) Notice: Subject to any disclaimer, the term of this patent is extended or adjusted under 35 U.S.C. 154(b) by 0 days.

(21) Appl. No.: 18/006,453

(22) PCT Filed: Jun. 17, 2022

(86) PCT No.: PCT/IB2022/055659

§ 371 (c)(1),
(2) Date: Jan. 23, 2023

(87) PCT Pub. No.: WO2023/242621

PCT Pub. Date: Dec. 21, 2023

(65) Prior Publication Data

US 2024/0087684 A1 Mar. 14, 2024

(51) Int. Cl.

*G16B 40/00* (2019.01)
*C07K 16/00* (2006.01)
*C12N 15/10* (2006.01)
*G06N 3/08* (2023.01)
*G16B 5/00* (2019.01)

(52) U.S. Cl.

CPC ........... *G16B 40/00* (2019.02); *C07K 16/005* (2013.01); *G16B 5/00* (2019.02); *C12N 15/1037* (2013.01); *G06N 3/08* (2013.01)

(58) Field of Classification Search

None
See application file for complete search history.

(56) References Cited

U.S. PATENT DOCUMENTS

2011/0119212 A1 5/2011 Hasey et al.
2021/0369798 A1 12/2021 Morales et al.

OTHER PUBLICATIONS

Aggarwal et al. An Ensemble Method for Designing Phage-Based Therapy against Bacterial Infections. NewsRX LLC, 2022. Print (Year: 2022).*

Piotr Tynecki, Arkadiusz Guziński, Joanna Kazimierczak, Michał Jadczuk, Jarosław Dastych, Agnieszka Onisko bioRxiv 2020.07.11. 198606; doi: https://doi.org/10.1101/2020.07.11.198606 (Year: 2020).*

Díaz-Galián MV, Vega-Rodríguez MA, Molina F. PhageCocktail: An R package to design phage cocktails from experimental phage-bacteria infection networks. Comput Methods Programs Biomed. 2022;221:106865. (Year: 2022).*

Zielezinski, A., Barylski, J. & Karlowski, W.M. Taxonomy-aware, sequence similarity ranking reliably predicts phage-host relationships. BMC Biol 19, 223 (2021). (Year: 2021).*

Menor-Flores M, Vega-Rodríguez MA, Molina F. Computational design of phage cocktails based on phage-bacteria infection networks. Comput Biol Med. 2022;142:105186. (Year: 2022).*

Li C, Shi T, Sun Y, Zhang Y. A Novel Method to Create Efficient Phage Cocktails via Use of Phage-Resistant Bacteria. Appl Environ Microbiol. 2022;88(6):e0232321. doi:10.1128/aem.02323-21 (Year: 2022).*

Abedon ST, Danis-Wlodarczyk KM, Wozniak DJ. Phage Cocktail Development for Bacteriophage Therapy: Toward Improving Spectrum of Activity Breadth and Depth. Pharmaceuticals (Basel). 2021;14(10):1019 (Year: 2019).*

Kimminau, E.A et al. "Bacteriophage In-Feed Application: A Novel Approach to Preventing Salmonella Enteritidis Colonization in Chicks Fed Experimentally Contaminated Feed." Journal of applied poultry research 29.4 (2020): 930-936. Web. (Year: 2020).*

Kortright, Kaitlyn E et al. "Phage Therapy: A Renewed Approach to Combat Antibiotic-Resistant Bacteria." Cell host & microbe 25.2 (2019): 219-232. Web. (Year: 2019).*

Haines, Melissa E K et al. "Analysis of Selection Methods to Develop Novel Phage Therapy Cocktails Against Antimicrobial Resistant Clinical Isolates of Bacteria." Frontiers in microbiology vol. 12 613529. Mar. 29, 2021, doi:10.3389/fmicb.2021.613529.

Ateba, C.N.; Akindolire, M.A. "Isolation and Characterisation of Bacteriophages with Lytic Activity Against Virulent *Escherichia coli* O157:H7: Potential Bio-Control Agents". Preprints 2019, 2019010132 (doi: 10.20944/preprints201901.0132.v1).

(Continued)

*Primary Examiner* — Anna Skibinsky
*Assistant Examiner* — Joseph Pulliam
(74) *Attorney, Agent, or Firm* — LUCAS & MERCANTI, LLP

(57) ABSTRACT

Methods and systems for designing phage therapy cocktails. A candidate phage selector module may be configured to predict lytic activity of phages using a first trained machine learning algorithm, and select candidate phages based at least in part on predicted lytic activity. A cocktail generator module may be configured to generate a set of phage cocktails using a second trained machine learning algorithm, based at least in part on predicted lytic activity. A feedback panel module may be configured to receive feedback information associated with phage cocktails, and use the feedback information to train the first and/or second trained machine learning algorithms.

28 Claims, 5 Drawing Sheets

(56) References Cited

OTHER PUBLICATIONS

Molina et al. "A New Pipeline for Designing Phage Cocktails Based on Phage-Bacteria Infection Networks". Front. Microbiol. 12:564532. doi: 10.3389/fmicb.2021.564532.

International Search Report dated Nov. 4, 2022 of Patent Cooperation Treaty application No. PCT/IB2022/055659 (13 pages).

Written Opinion for Corresponding International Application No. PCT/IB2022/055659 dated Nov. 4, 2022 (8 pages).

* cited by examiner

METHODS AND SYSTEMS FOR DESIGNING PHAGE COCKTAILS

CROSS REFERENCE TO RELATED APPLICATION

This Application is a 371 of PCT/IB2022/055659 filed on Jun. 17, 2022, which is incorporated herein by reference.

FIELD

The present disclosure relates to the field of antibacterial agents and artificial intelligence.

BACKGROUND

In recent years, the proliferation of antibiotic-resistant bacteria has become one of the most challenging and serious problems for public health [1]. The use of antibiotics has been frequently used by modem medicine to ameliorate or cure life-threatening bacterial infections. However, the ability of bacteria to mutate in a short time may allow the development of antibiotic-resistant bacterial strains [2]. The increase of treatments with these drugs and the inadequate use of them to treat non-bacterial diseases may cause significant challenges arising from the proliferation of antibiotic-resistant bacteria [3].

SUMMARY

Antibiotic resistance may be one of the greatest threats to world health. Bacteriophage viruses may be used as a natural alternative to fight various bacterial infections when classical treatment using antibiotics is inefficient.

The use of bacteriophages or phages to inhibit bacterial growth may be a tool of growing interest as an alternative treatment to antibiotics, especially in the food industry. Bacteriophages (or phages) may correspond to viruses capable of solely and exclusively invading bacteria [4]. Bacteriophages may be natural antagonists of bacteria, therefore, they may regulate the ecosystem by limiting the abundance of their hosts through lytic infections [5]. In order to "survive", phages may be required to specifically recognize a bacterium, enter its interior, and use its cellular machinery to be able to produce copies of itself. As used herein, the term "phage therapy" generally refers to the use of bacteriophages or a mixture of them against pathogenic bacteria [6].

In phage therapy, the use of phage cocktails as an antibacterial agent may be a common practice to enhance bactericidal activity while decreasing the likelihood of hosts developing resistance to multiple phages simultaneously. Rational cocktail design may be one of the key elements for successful phage therapy [7].

Knowing the bacteriophage-host interaction and designing an appropriate formulation may be vital to determine a suitable treatment to different bacterial populations. However, searching for and characterizing bacteriophages that infect specific hosts may be a laborious and time-consuming task, carried out by one-to-one experiments and manual annotation of the interactions between samples. Moreover, only 1% of bacterial hosts may have been successfully cultured in the laboratory, thereby limiting the detection and characterization of the phage-host relationship. In addition, there are some examples that demonstrate certain situations where two phages that each individually have a good host range on certain bacterial isolates independently, when combined in a cocktail, do not maintain their efficacy when administered in a combination or mixture. In some cases, these bacteriophages interfere with each other, and this interaction may be a priori unpredictable.

Thus, the search for optimal phage combinations to assemble a cocktail capable of covering a broad spectrum of hosts may be a challenging and complex task, such as when working with a large number and variety of phages. Therefore, it may be necessary to develop improved tools to accelerate the testing and search for phages suitable for creating phage therapy cocktails.

The effectiveness of phage-based therapies may be confirmed empirically, and therefore, there is a growing demand for methods and systems for modeling genomic data and predicting phage-host interactions without the need for extensive experimentation. Although there are developments with promising results in public databases and under limited testing conditions, such methods may not be incorporated and tested on an industrial scale under real production conditions.

The use of Artificial Intelligence (AI), machine learning (ML), and Cloud Computing may enable creation of advanced analytical tools on digital platforms that allow the integration and automation of low cost AI algorithms and with high scalability. For example, algorithms may be developed to predict the interaction between bacteria and certain molecules at high accuracy and throughput, to accelerate innovation and drug development.

Therefore, there is a need to develop methods and systems for advanced analytics based on Artificial Intelligence for the accurate, high-throughput design of cocktails used in phage therapy, which may accelerate the study of bacteriophage-host interactions and the optimization of the bacteriophages used in each formulation.

In some aspects, the present disclosure provides systems and methods based on artificial intelligence for the automatic design of bacteriophage cocktails for phage therapy, which may allow determining the best phages and predicting their bactericidal activity in silico against a group of bacteria, when said phages are combined in a bacteriophage cocktail. This system may aim to accelerate the study of bacteriophage-host interactions and the optimization of the selection of phages used in each formulation. The system may learn from internal and external free-use databases, determining relationships between phages and bacteria at the genetic level and optimizing the set of compatible phages to use in each formulation.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides a system of advanced analytics and methods based on artificial intelligence for the automatic design of cocktails for phage therapy. Such automatic design may comprise optimally determining the best phages and predicting in silico their bactericidal activity in a cocktail of bacteriophages, when considering various criteria, such as criteria that ensure that these bacteriophages do not interfere with each other during their action on the pathogens. The formulated cocktails with the systems and methods of the present disclosure may possess high bactericidal activity on a group of host bacteria based on the knowledge of the phage-host interaction.

In an aspect, the present disclosure provides a system of advanced analytics based on Artificial Intelligence for the design of cocktails used in phage therapy. This system aims to accelerate the study of bacteriophage-host interactions and the optimization of the bacteriophages used in each formulation, arriving at optimized formulations (e.g., having a minimum number of phages possible while maximizing the host range). The system may learn from data retrieved from internal and external free-use databases, determining the relationship between phages and bacteria at the genetic level, and optimizing the set of compatible phages to use in each formulation.

Figure 1:
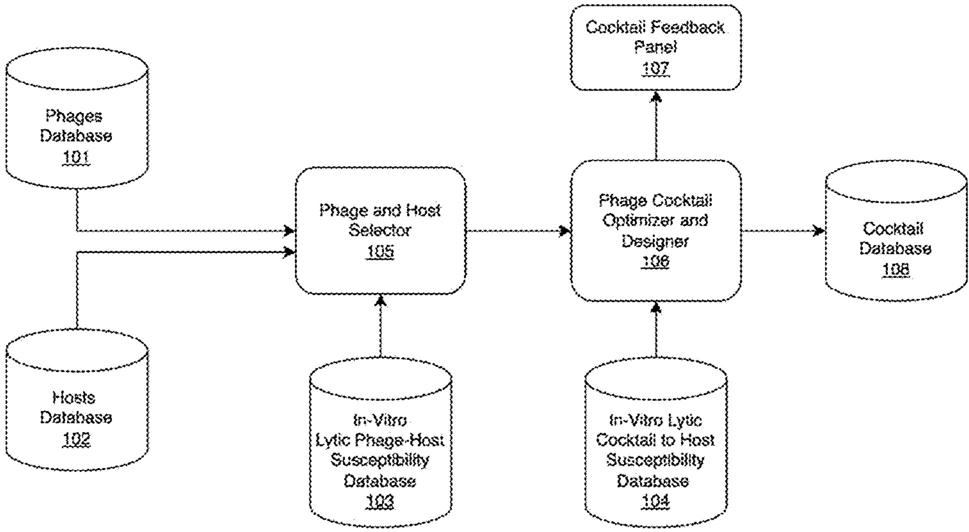
FIG. 1 illustrates a diagram of various stages and elements of an example of a system for phage therapy cocktail design.

FIG. 1 illustrates a diagram of an example of a system of the present disclosure. In some embodiments, the system comprises the following modules:

1. a candidate phage selector (105) which allows in silico estimation of those phages most likely to produce lysis in a group of bacterial isolates;
2. a cocktail generator (106) which allows selection of the optimal phages and establishing the best combination of phages in each cocktail according to various criteria, such as bacterial isolates and biological criteria;
3. a feedback panel (107) which allows the system to receive feedback, such as information from users in the laboratory, and to improve formulations.

In some embodiments, the system comprises the following stages:

a) receive data from phage databases (101) and host databases (102):
b) select phages and hosts (105);
c) optimize and design phage cocktails (106);
d) send data obtained by the system to a cocktail database (108).

The system learns from data retrieved from internal and external free-use databases. The data used may allow quantitative and qualitative characterization of bacterial and viral isolates. These data may comprise nucleotide sequences, amino acid sequence annotation, pangenome and allelic variants (SNP) of phages (101) and hosts (102), in vitro experiments to assess individual phage-host lytic susceptibility (103), in vitro experiments to assess cocktail-host lytic susceptibility (104), or any other related data. The database can be implemented using memory, for example, random access memory (RAM), electrically erasable programmable read-only memory (EEPROM), flash memory, hard disk drives, optical disk drives, solid state drives or any type of memory suitable for database storage.

Methods of cocktail elaboration may comprise predicting the interaction between bacterial isolates and phages. This evaluation may aim to determine the individual bactericidal activity of each phage on each host to evaluate the feasibility of being used in a cocktail. A method or system may use Machine Learning to predict bacterial interaction at the individual level to discard early on phages that are not candidates for in vitro testing. Such ML algorithms may learn from data retrieved from databases to recognize patterns and to determine relationships between the genomic profile of hosts and phages. In this way, a trained machine learning algorithm may be used to predict whether at least one phage from a given collection has lytic activity on that bacterium. These databases of in vitro experimental data can be open access or internal databases.

In some embodiments, the candidate phage selector module further allows in silico selection of those bacterial isolates that are representative of a large number of samples.

This stage includes various operations for the selection of candidate bacteriophages and representative bacterial isolates in the collected samples.

Figure 2:
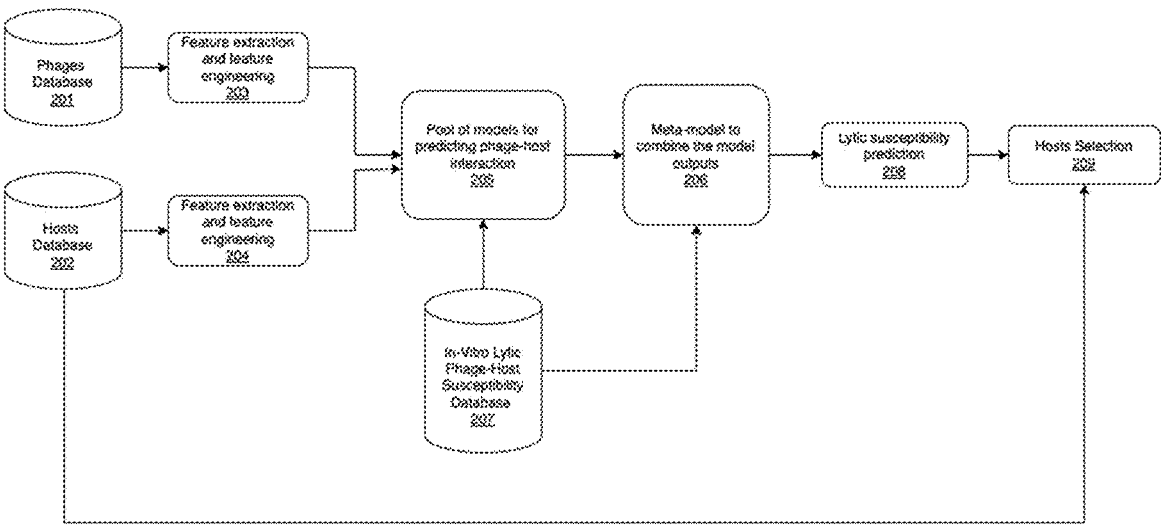
FIG. 2 illustrates a diagram of various stages of an example of a candidate phage selector module.

In some embodiments, a candidate phage selector module is provided. FIG. 2 illustrates a diagram of an example of the candidate phage selector module.

In some embodiments, the candidate phage selector module comprises the following stages:

a) read data from phage databases (201) and host databases (202);

b) extract and perform attribute engineering on input data (203, 204);

c) predict the lytic susceptibility of each host to each phage using a trained machine learning model (205, 208);

d) select phages and hosts (209).

Optionally, the candidate phage selector module uses a meta-model (206), which may be generated by combining results of a plurality of different models (e.g., obtained in operation c).

The candidate phage selector module recommends a set of the most suitable bacteriophages to form a bacteriophage cocktail. This realization may comprise determining in silico the susceptibility of each isolate or host to a phage, and is able to alert in case there are not enough or no phages in the collection that possess lytic activity on the isolates of the system.

The algorithms analyze attribute data related to the characterization of genomic profile of phages (201) and hosts (202). These attributes may correspond to types of data that serve to characterize the species under analysis, such as nucleotide sequences, amino acid sequences, genomic profiling, pangenome, single nucleotide polymorphism (SNP), virulence factors, antibiotic resistance factors. Further, the training of the model(s) utilizes the measurement of the susceptibility of each host to a given phage (207), such as through host range on Double Layer Agar and/or bacterial growth curves at OD600, or other suitable techniques to determine phage-host interactions.

The final phage recommendation (208) is the result of inference from one or more non-trivially combined classifiers. Models at this stage predict whether phages are suitable for phage therapy by evaluating different data domains. The families of models involved in this stage can be, but are not restricted to, Random Forest, Support Vector Machines, XGBoost, Logistic Regression, Deep Neural Networks (DNN), Recurrent Neural Networks (RNN), Bayesian Neural Networks, Bayesian Matrix Factorization (BMF), Bayesian Regression, Reinforcement Learning, and/or any other method related to machine learning and artificial intelligence.

In some embodiments, it is desirable to reduce the set of isolates to a subset thereof that allows the entire system to be represented. In some embodiments, the set of hosts susceptible to the phages in the collection that have been recommended by the selector in the previous step are selected. During the selection it may be necessary to identify similar hosts under some criteria using techniques such as Hierarchical Clustering (HC), Density-based clustering, Bipartite Recursively Induced Modules (BRIM). In some cases it will also be necessary to reduce the dimensionality by any suitable dimensionality reduction technique, such as Principal Components Analysis, Manifold Learning. Autoencoders and/or any other method or technique related to machine learning or artificial intelligence. In some embodiments, the model can be trained without any feature compression techniques.

Figure 3:
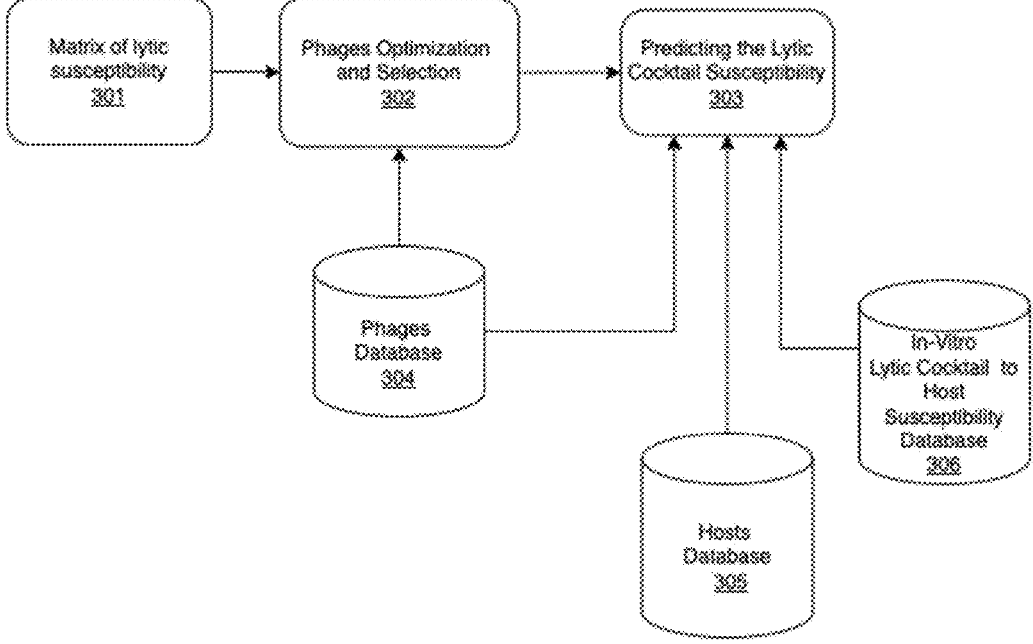
FIG. 3 illustrates a diagram of various stages of an example of a cocktail generator module.

In some embodiments, the system comprises a cocktail generator module. FIG. 3 illustrates a diagram of an example of the cocktail generator module.

In some embodiments, the cocktail generator module comprises the following stages.

a) receive data from phage-host lytic susceptibility matrix databases (301) and phage databases (304);

b) optimize and select phage cocktails (302);

c) predict the lytic susceptibility of each host to the cocktail (303).

This procedure aims to search for a set of the N best phages that optimize the success of a cocktail of size N, according to a set of rules and performance metrics. One such rule, for example, may be to ensure sufficient genetic diversity among the selected phages.

In some embodiments, an algorithm performs an optimization and selection of the phages (302), removing those that do not contribute to the success of the cocktail. In some embodiments, the optimization may use sampling of subsets of phages to speed up the search. Examples of the techniques suitable for use in this algorithm include: Bayesian Optimization, Bayesian Regression, Linear Programming, Particle Swarm Optimization (PSO), Genetic Algorithms (GA), Association Rules (e.g. Apriori and FP-Growth), Reinforcement Learning, and/or other suitable techniques.

The input of this module corresponds to a matrix with host/phage interactions (301). The module may consider as input the susceptibility matrix predicted in the previous phage selector module, for the selected phages and hosts. In some cases, the module may also use an in vitro estimated lytic susceptibility matrix (306). In some cases, the module analyzes as inputs only the genetic profile of the selected phages (304) and hosts (305).

The information on the interaction between bacteriophages and hosts is contained in two matrices:

Host range matrix with the qualitative value of the observed lytic activity, in the range [0, 3] and/or in the range [0, 4].

Binary host range matrix: interaction (1), and no interaction (0).

The binary host range matrix is constructed from the qualitative values, considering as interaction a lytic activity greater than or equal to 1. Both host range matrices have dimension nh host rows by nph phage columns.

The output of the optimization algorithm corresponds to a set of candidate phage cocktails that meet the selection metrics.

Figure 4:
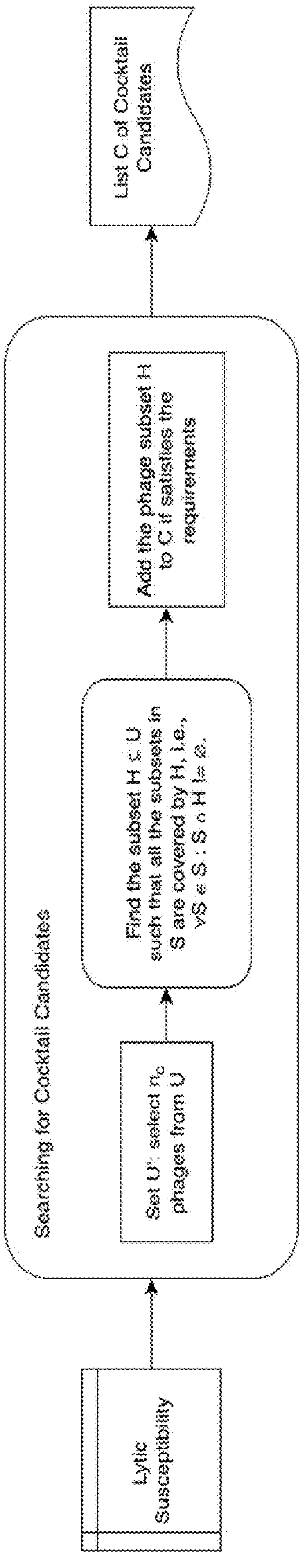
FIG. 4 illustrates a diagram of the optimization and selection stage of phage cocktails.

In some embodiments, the system comprises a stage of optimizing and selecting phage cocktails. FIG. 4 illustrates a diagram of examples of the processes described in the cocktail optimization and selection stage. Given a system (U, S), where U corresponds to all the elements of the universe of phage-host interactions and S corresponds to a collection of subsets of U, the algorithm finds the smallest subset of the universe $H \subseteq U$ such that all sets in S are spanned by H, i.e. $\forall S \in S: S \cap H \, != \emptyset$.

For a binary matrix of host range U and a set of candidate phage cocktails C, the algorithm may comprise the following operations:

1. initialize the set of candidate phage cocktails C;
2. select nc phages randomly from set U→set U';
3. find the set of phages H satisfying the problem definition for U' subject to various constraints, such as maximum and minimum phage number, coverage, and genetic diversity;
4. add the set of phages H to the set of candidate phage cocktails C if it meets the criteria established for optimization.

In some embodiments, it is desirable to group the phages into subsets in which pre-determined conditions of interest for the cocktail elements are verified. This sampling method may avoid an exhaustive search, thereby providing a more efficient exploration of the solution space.

In some embodiments, base constraints are considered for performing the search. More specifically, in some embodiments, the base constraints for searching include criteria such that each host must have at least one interaction (e.g., lytic susceptibility) with at least one of the phages in the cocktail. In some embodiments, the genetic diversity of the cocktail components is considered as a base constraint for searching. For example, this similarity may be estimated using a matrix comprising the distance between DNA sequences of the phages, thereby enabling them to be grouped according to their similarity degree. Specifically, similarity degree between phages can be estimated using an identity matrix that quantifies the distance between phage DNA sequences. Thus, phages with a similarity greater than or equal to a pre-determined threshold are considered to belong to the same group or as not genetically diverse, and phages with a similarity below the pre-determined threshold are considered to belong to different groups or as genetically diverse. The methods and pre-determined thresholds for assessing similarity between phages may vary.

In some embodiments, it is considered as a base constraint that the phages are genetically diverse from each other, and the number of phages in the cocktail is the minimum possible while maximizing the host range to be possessed by the phage.

More specifically, in some embodiments, the threshold is defined at 95% sequence identity. Thus, phages with a similarity greater than or equal to 95% are considered to belong to the same group or as not genetically diverse.

The final selection of phages in the formulation may follow a set of learned rules that are related to the nature of the samples. The selection can be performed manually by an operator, by machine learning or artificial intelligence techniques, or by a combination of automatic and manual processing.

In some embodiments, once the phages and hosts have been selected, an algorithm generates a set of recommended cocktails that have the highest likelihood (e.g., probability) of eliminating the hosts selected in the previous stage and evaluates the likelihood (e.g., probability) of success of each cocktail.

In some embodiments, the system comprises a stage of predicting the cocktail lytic susceptibility (303). At this stage, an algorithm predicts the lytic activity of each cocktail on the isolates under analysis. In such a realization, lytic activity can be predicted using genetic profile of phages (304) and hosts (305) or other similar types of data to characterize the species under analysis.

The input of this stage corresponds to the set of cocktails with N phages resulting from the selection process (302). It also receives as input, results of lytic activity for previous cocktails (306), the genetic profile of the phages (304) and of the hosts (305), or other similar data to characterize the species under analysis.

Examples of the techniques used in this stage include: Random Forest, Logistic Regression, Support Vector Machines, XGBoost, Logistic Regression, Deep Neural Networks (DNN), Recurrent Neural Networks (RNN), Bayesian Neural Networks, Bayesian Regression, Reinforcement Learning, Graph Neural Networks, or any other suitable method related to machine learning or Artificial Intelligence.

The output of this stage is a set of candidate phage cocktails with their respective predicted lytic activity for each isolate.

In some embodiments, the system comprises a feedback panel module comprising the following stages:

a) visually present the cocktail formulations obtained (e.g., on a user interface to a laboratory user);
b) select cocktails of interest;
c) direct further in vitro testing of selected cocktails;
d) receive and incorporate feedback to the system for readjustment of parameters, thereby training the system.

At the end of the optimization and cocktail design module, the candidate phage cocktail information can be visually presented to the users (e.g., who perform in vitro formulation development and testing). This panel may have the following objectives:

1. Increase human analysis capabilities by presenting indicators for each formulation in order to provide users with the maximum information to select the most suitable cocktails.
2. Request new in vitro experiments from the user for those formulations that are viable but for which the system has a low reliability.
3. Allow the user to change algorithm parameters to correct predicted formulations if necessary.
4. Request feedback from in vitro tests to readjust models for future formulations.

Figure 5:
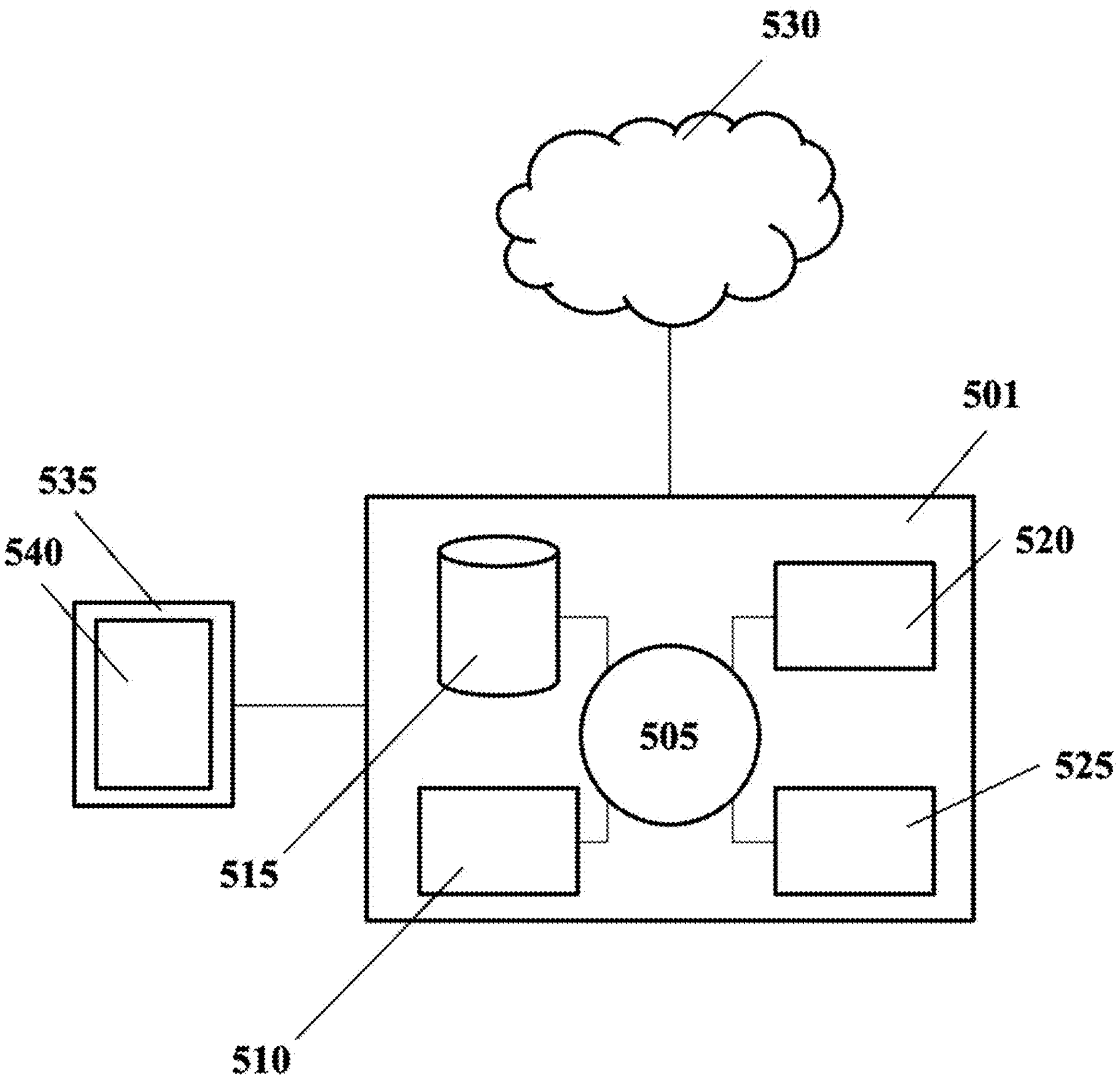
FIG. 5 shows a computer system that is programmed or otherwise configured to implement methods provided herein.

The present disclosure provides computer systems that are programmed to implement methods of the disclosure. FIG. 5 shows a computer system 501 that is programmed or otherwise configured to perform analysis or operations of the methods. The computer system 501 can regulate various aspects of methods and systems of the present disclosure, such as, for example, perform an algorithm, input training data, analyze feature sets, or output results of an algorithm. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries, and saved programs. The storage unit 515 can store user data. e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a medical professional or patient). Examples of remote computer systems include personal computers (e.g., portable PC), slate or tablet PC's (e.g., Applet iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM. DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, an input of data, or an visual output relating to an algorithm. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, analysis or operations of methods of the present disclosure.

In an aspect, the present disclosure provides a method of phage selection for phage therapy cocktails, comprising the following stages:

a) receive data from phage and host databases;

b) extract and perform attribute engineering on the input data c) predict the lytic susceptibility of each bacterium to each phage using a machine learning model;

d) select phages and hosts.

Optionally, the candidate phage selector module combines the results of different models obtained in operation c) using a meta-model.

In some embodiments, it is desirable to reduce the set of isolates to a subset thereof that allows the entire system to be represented. In some embodiments, the method can be performed without performing a feature compression technique.

The algorithms in this method may analyze attribute data related to the characterization of the genomic profile of phages and hosts. These attributes can correspond to various types of data to characterize the species under analysis, such as nucleotide sequences (e.g., DNA or RNA), amino acid sequences, genomic profile (pangenome), and single nucleotide polymorphisms (SNPs). Further, the training of the model(s) uses phage-host interaction data, such as growth curves at OD600 nm, double-layer Agar, or other suitable techniques.

In an aspect, the present disclosure provides a method for generating cocktails for phage therapy comprising the following stages:

- a) receive data from a phage-host lytic susceptibility matrix and phage databases;
- b) optimize and select phage cocktails;
- c) predict the lytic susceptibility of each host to the cocktail.

The method considers as input information a host/phage interactions matrix. The output information of said method comprises a set of candidate phage cocktails that meet a set of selection metrics.

In some embodiments, the method comprises a stage of optimizing and selecting cocktails for phage therapy. For a binary matrix of host range U and a set of candidate cocktails C, the stage of optimization and selection of cocktails for phage therapy may comprise the following operations:

1. initialize the set of candidate phage cocktails C;
2. select nc phages randomly from set U→set U';
3. find the set of phages H satisfying the problem definition for U' subject to various constraints, such as maximum and minimum phage number, coverage, and genetic diversity;
4. add the set of phages H to the set of candidate phage cocktails C if it meets the criteria established for optimization.

In some embodiments, it is desirable to group phages into subsets in which pre-determined conditions of interest for the cocktail elements are verified. This sampling method may avoid an exhaustive search, thereby providing a more efficient exploration of the solution space.

In some embodiments, base constraints are considered to perform the search. More specifically, in some embodiments, the base constraint for include criteria such that each host must have at least one interaction (e.g. lytic susceptibility) with at least one of the phages in the cocktail. In some embodiments, the genetic diversity of the cocktail components is considered as a base constraint for searching. For example, this similarity may be estimated using a matrix comprising the distance between DNA sequences of the phages, thereby enabling them to be grouped according to their similarity degree. Specifically, similarity degree between phages can be estimated by using an identity matrix that quantifies the distance between phage DNA sequences. Thus, phages with a similarity greater than or equal to a pre-determined threshold are considered to belong to the same group or as not genetically diverse, and phages with a similarity below the pre-determined threshold are considered to belong to different groups or as genetically diverse. The methods and pre-determined thresholds for assessing similarity between phages may vary.

In some embodiments, it is considered as a base constraint that the phages are genetically diverse from each other, and the number of phages in the cocktail is the minimum possible while maximizing the host range to be possessed by the phage.

More specifically, in some embodiments, the threshold is defined at 95% sequence identity. Thus, phages with a similarity greater than or equal to 95% are considered to belong to the same group or as not genetically diverse.

In some embodiments, the method comprises a stage of predicting the lytic susceptibility of the cocktail. In this stage, the lytic activity of each cocktail on the isolates under analysis is predicted. In this realization, lytic activity can be predicted using the genetic profile of the phages in the cocktail and their hosts or other similar data to characterize the species under analysis.

In an aspect, the present disclosure provides method for generating phage therapy cocktails using a feedback panel, comprising the following stages:

- a) visually present the cocktail formulations obtained (e.g., on a user interface to a laboratory user);
- b) select cocktails of interest;
- c) direct further in vitro testing of selected cocktails;
- d) receive and incorporate feedback to the system for readjustment of parameters, thereby training the system.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1. Construction of a Candidate Phage Selector Module

Using systems and methods of the present disclosure, a candidate phage selector module was constructed as follows. For the candidate phage selector module, bacteriophage-host interaction information was obtained from the bacterial lytic susceptibility analysis, using two matrices:

1. Host range matrix with qualitative value of lytic activity observed, in rank [0,4].
2. Binary host range matrix, interaction or non-interaction, in range [0,1].

The binary host range matrix was constructed from the qualitative values, considering as interaction a lytic activity greater than or equal to 1. The system analyzed as input the binary host range matrix to identify the interaction between phage and host.

Further, the candidate phage selector module received data from the bioinformatics analysis, such as nucleotide sequences and/or amino acid sequences for phage and host characterization. With the training data comprising interactions between phage and host, a set of ML models was trained, and the best performing model was selected in a cross-validation evaluation by identifying patterns between the genomic profile of isolates and phages. The selected model was a Random Forest (F-score=0.8), which was trained to predict the interaction between new hosts and phages. After the algorithm predicted the lytic susceptibility of new isolates, it was converted to a host range matrix. This result served as input for the cocktail design algorithm and the host selection algorithm, which aimed to reduce the number of isolates used in in vitro tests for verification of actual lytic susceptibility. In the case of host selection, a hierarchical clustering was performed on the predicted host range matrix, from which a representative sample was selected from each cluster. Analysis of the results by in vitro tests showed that the prediction of lytic susceptibility for the new isolates enabled sensitive detection of 73% of the real phage-host interactions (e.g., presences) and specific detection of 88% of the real phage-host interaction absences. The overall performance of the model for predicting lytic susceptibility for new hosts was an accuracy of 83%.

Example 2. Construction of a Cocktail Generator Module

Using systems and methods of the present disclosure, a cocktail generator module was constructed as follows. The cocktail generator module analyzed as input data the individual host lytic susceptibility to phages. Further, it received data from phages and hosts genomic characterization.

Let U be the universe of phage-host interactions and S be a collection of subsets of those interactions. The cocktail generator module found a set of candidate phage cocktails C by solving the following problem:

Given a system (U, S), where U corresponds to all elements of the universe of interactions and S corresponds to a collection of subsets of U, the algorithm finds the smallest subset of the universe H F U such that all sets in S are spanned by H, i.e., $\forall S \in S: S \cap H \mathrel{!}= \emptyset$.

In order to evaluate a large number of phages, the cocktail generator module performed a total of 50,000 iterations, and the phage sets were searched for using the following procedure:

a) initialize the set of candidate phage cocktails C;
b) select nc phages randomly from set U→set U';
c) find the set of phages H satisfying the problem definition for U' subject to various constraints, such as maximum and minimum phage number, coverage, and genetic diversity;
d) add the set of phages H to the set of candidate phage cocktails C if it meets the criteria established for optimization.

The cocktail generator module considered the genetic diversity constraint of the phage cocktail by quantifying a distance metric between phage DNA sequences. Thus, phages with a similarity equal to or higher than a pre-determined threshold were grouped together. Therefore, phages with a similarity less than the pre-determined threshold were placed into different groups. A pre-determined threshold of 95% sequence identity was used. From the result in the optimization stage, diverse cocktails were selected in which all the phages in the cocktail belong to different groups. Also, the cocktail generator module considered the constraint by cocktail size, limiting the number of phages to N=5.

Finally, the algorithm estimated different success metrics and used them to rank the candidate phage cocktails for selection for subsequent in vitro testing.

Example 3. Construction of a Feedback Panel Module

Using systems and methods of the present disclosure, a feedback panel module was constructed as follows. The set of cocktails designed by the system was analyzed by a professional laboratory team, which selected a subset of cocktails according to a set of metrics, such as those cocktails that had a higher average individual percentage inhibition, and evaluated the subset of cocktails by in vitro assays for measuring bacterial growth inhibition. The results of these assays were fed back to the system to correct the cocktail estimates generated by the system (e.g., the cocktail generator module), thereby training the system, and to request new assays. For example, the optimization or training may comprise minimizing a loss function (e.g., a difference between estimated outcomes and observed outcomes). Further, the new cocktails were incorporated to the internal database to evaluate the success of future candidate phage cocktails.

Example 4. Automatic Design of Phage Therapy Cocktails

Using systems and methods of the present disclosure, a total of 258 novel hosts were challenged against 47 phages in the collection. For analysis purposes, the cocktail design system analyzed as inputs data retrieved from a database of individual phage-host interactions on double-layer Agar and the genomic characterization of each species in the database and novel species in the challenge.

The automatic design of phage therapy cocktails was constrained to maximize genetic diversity among the phages of the cocktail and to limit the maximum cocktail size to N=5 phages.

Using the phage-host interaction and genomic characterization databases, a set of machine learning models were trained to recognize patterns between the genomic profile of the species and their lytic susceptibility. A binary host range matrix was used to represent lytic susceptibility. The model with the highest cross-validation performance was selected and used for prediction of new isolates. A Random Forest model was observed to achieve the highest performance (F-score=0.81). The model used can be replaced by another model as needed to achieve improvements in predictive performance.

The trained model predicted lytic susceptibility as a host range matrix for the 250 novel hosts. The results were analyzed using the host selector module to obtain a sample of 138 representative bacteria from the system. The predicted lytic susceptibility for this subset of hosts was tested in vitro. This in vitro lytic susceptibility data was analyzed using the cocktail design module.

The cocktail design module optimized phage-host relationships by searching for phage sets through the following procedure:

a) initialize the set of candidate phage cocktails C;
b) select nc phages randomly from set U→set U';

c) find the set of phages H satisfying the problem definition for U' subject to various constraints, such as maximum and minimum phage number, coverage, and genetic diversity;

d) add the set of phages H to the set of candidate phage cocktails C if it meets the criteria established for optimization.

As a result, this module produced 47,937 phage combinations, with 164 combinations of 3 phages, 1,660 combination of 4 phages, and 9,474 combinations of 5 phages. For testing purposes, the larger size cocktails included the smaller size cocktails. Of these, only 23,181 formulations satisfied the genetic diversity constraint. For each cocktail, the algorithm reported a metric of the bactericidal activity of the cocktail, calculated as the average of the individual bactericidal activity of the selected phages. In addition, the results reported the percentage coverage of the resulting matrix (fill) and whether or not the cocktail is genetically diverse.

The in vitro lytic activity of the 6 phage cocktails with the best matrix coverage recommended by the system was evaluated in a laboratory. The results of this experimentation were compared with the lytic score predicted by the system, as shown in Table 1.

TABLE 1

Observed in vitro effectiveness (percentage) and lytic score of the phage cocktails designed using a system of the present disclosure.

| Cocktail | Set of Phages | Effectiveness % (observed in vitro) | Lytic score (predicted) |
|---|---|---|---|
| Cocktail 1 | Phage A, Phage B, Phage C, Phage D, Phage E | 60.21 | 1.67 |
| Cocktail 2 | Phage A, Phage B, Phage C, Phage D, Phage F | 62.04 | 1.67 |
| Cocktail 3 | Phage A, Phage B, Phage D, Phage E, Phage G | 62.57 | 1.70 |
| Cocktail 4 | Phage A, Phage B, Phage D, Phage G, Phage F | 64.92 | 1.70 |
| Cocktail 5 | Phage A, Phage B, Phage E, Phage H | 67.54 | 1.71 |
| Cocktail 6 | Phage A, Phage B, Phage F, Phage H | 69.90 | 1.71 |

From the results obtained, it was observed that the percentage of in vitro effectiveness increases as the predicted lytic score for the phage cocktails increases. Additionally, the in vitro lytic activity of a phage Cocktail that was not recommended by the algorithm, which did not present genetic diversity, was evaluated. The results indicated that this cocktail exhibited significantly lower lytic activity compared to the cocktails that were designed and recommended by the system.

The results demonstrated that the system was able to automatically design phage therapy cocktails having high concordance between predicted lytic score and observed in vitro effectiveness, and indicates that the system may be used to contribute to the design of other formulations by reducing the analysis and search time of its components.

REFERENCES

[1] Prada-Peñaranda C. Holguin-Moreno A V, Gonzalez-Barrios A F, Vives-Flórez MJ (2015) Fagoterapia, alternativa para el control de las infecciones bacterianas. Perspectivas en Colombia. Universitas Scientiarum 20(1): 43-60 doi: 10.11144/Javeriana.SC20-1.faci is incorporated by reference herein in its entirety.

[2] O'neill, J. (2014). Antimicrobial resistance. Tackling a crisis for the health and wealth of nations is incorporated by reference herein in its entirety.

[3] "La siguiente pandemia ya ha empezado: la covid ha acelerado la aparición de superbacterias". El País. Noviembre, 2021.

[4] Maniloff, J., Desselberger, U., & Ball, L. A. (2005). Virus taxonomy: VIIIth report of the International Committee on Taxonomy of Viruses is incorporated by reference herein in its entirety.

[5] Clara Torres-Barceló and Michael E Hochberg. Evolutionary rationale for phages as com-plements of antibiotics. Trends in microbiology, 24 (4): 249-256, 2016. is incorporated by reference herein in its entirety.

[6] Lin, D. M., Koskella, B., Lin, H. C. (2017). Phage therapy: An alternative to antibiotics in the age of multi-drug resistance. World J Gastrointest Pharmacol Ther. 6:8(3):162-173 is incorporated by reference herein in its entirety.

[7] Merabishvili, M., Pirnay. J. P., & De Vos, D. (2018). Guidelines to compose an ideal bacteriophage cocktail. In Bacteriophage therapy (pp. 99-110). Humana Press, New York, NY is incorporated by reference herein in its entirety.

What is claimed is:

1. A computer-implemented method for designing phage therapy cocktails, method comprising:

(a) predicting, with a candidate phage selector, a predicted lytic activity of each of a plurality of phages with a first trained machine learning algorithm, and selecting a plurality of candidate phages from the plurality of phages based at least in part on the predicted lytic activity;

wherein (a) further comprises:

i) receiving input data comprising phage data of the plurality of phages and host data of a set of hosts;

ii) extracting attribute data from the input data;

iii) processing the attribute data using the first trained machine learning algorithm to predict lytic susceptibility of individual hosts from set of hosts to individual phages from the plurality of phages, thereby generating phage-host lytic susceptibility data; and iv) providing a selection of the plurality of phages from the plurality of phages and a selection of a set of candidate hosts from the set of hosts, based at least in part on the phage-host lytic susceptibility data, (b) generating, with a phage cocktail generator based on a second machine learning algorithm, the set of candidate phage cocktails selected in (a) (iv), wherein each phage cocktail of the set of candidate phage cocktails comprises a combination of at least two phages from a plurality of candidate phages, and wherein each phage cocktail of the set of candidate phage cocktails is generated based at least in part of the predicted lytic activity of the at least two phages, wherein the second machine learning algorithm uses as constraint the genetic diversity between phages; and wherein (b) further comprises:

a) receiving a phage-host lytic susceptibility matrix and phage data retrieved from phage databases;

b) selecting a plurality of candidate phage cocktails based at least in part on the phage host lytic susceptibility matrix and the phage data; and c) predicting lytic susceptibility of hosts to individual candidate phage cocktails from the plurality of candidate phage cocktails; and (c) visually presenting, by a feedback panel display, the generated set of phage cocktails from the set of candidate phage cocktails of (b) to a user interface to a user for selecting phage cocktails of interest from the generated set of candidate phage cocktails to conduct in vitro formulation development and testing for developing a plurality of developed phage cocktail formulations, and wherein the user receives the results obtained from the in vitro testing of the selected cocktails and inputs the results, by a feedback panel display, into at least one of the first trained machine learning algorithm and one of the second trained machine learning algorithm, and (d) outputting, by the feedback panel display, a developed phage cocktail formulation for subsequently in vitro verification;

(f) verifying the developed phage cocktail formulation by double layer agar;

(e) selecting the developed phage cocktail formulation of (d) based on a predetermined in vitro effectiveness percentage threshold, wherein the predetermined in vitro effectiveness percentage threshold is greater than 60.00, (g) generating the developed phage cocktail by repeating steps (a)-(e) for making developed phage cocktail formulations;

(h) making the developed phage cocktail formulations by a process that comprises double layer agar.

2. The method of claim 1, wherein (a) further comprises processing data from phage databases and host databases.

3. The method of claim 1, wherein (a) further comprises selecting a plurality of candidate phages and a set of candidate hosts.

4. The method of claim 1, further comprising storing data associated with the set of phage cocktails in a database.

5. The method of claim 1, further comprising learning from data retrieved from databases.

6. The method of claim 5, wherein the databases comprise free-use internal and external databases.

7. The method of claim 5, wherein the data retrieved from the databases comprises information corresponding to phage nucleotide sequences, host nucleotide sequences, phage amino acid sequence annotation, host amino acid sequence annotation, phage pangenome, host pangenome, phage allelic variants (SNPs), host allelic variants (SNPs), in vitro data assessing individual phage-host lytic susceptibility, in vitro data assessing cocktail-host lytic susceptibility, or a combination thereof.

8. The method of claim 5, wherein the databases are implemented using random access memory (RAM), electrically erasable programmable read-only memory (EEPROM), flash memory, hard disk drives, optical disk drives, solid state drives, or a combination thereof.

9. The method of claim 3, wherein selecting the plurality of candidate phages and the set of candidate hosts further comprises predicting individual lytic susceptibility between phages from the plurality of candidate phages and bacterial isolates.

10. The method of claim 9, wherein predicting the individual lytic susceptibility is performed using the first trained machine learning algorithm.

11. The method of claim 3, wherein selecting the plurality of candidate phages and the set of candidate hosts further comprises performing an in-silico selection of representative bacterial isolates from a set of samples.

12. The method of claim 1, wherein (a) further comprises using a meta-model comprising a combination of a plurality of different models.

13. The method of claim 1, wherein the first trained machine learning algorithm is configured to process attribute data related to genomic profiling characterization of phages and/or hosts.

14. The method of claim 1, wherein the attribute data corresponds to nucleotide sequences, amino acid sequences, genomic profiling, pangenome, single nucleotide polymorphism (SNP), virulence factors, antibiotic resistance factors, measurement of individual host-phage susceptibility, or a combination thereof.

15. The method of claim 1, wherein the first trained machine learning algorithm or the second trained machine learning algorithm comprises a Random Forest, Support Vector Machines, XGBoost, Logistic Regression, Deep Neural Networks (DNN), Recurrent Neural Networks (RNN), Bayesian Neural Networks, Bayesian Matrix Factorization (BFM), Bayesian Regression, Reinforcement Learning, or a combination thereof.

16. The method of claim 1, wherein the second trained machine learning algorithm processes individual phage-host lytic susceptibility matrix data, phage and host genetic profiling data, or a combination thereof.

17. The method of claim 16, wherein the individual phage-host lytic susceptibility matrix data is generated using the phage selector module or using in vitro data assessing individual phage-host lytic susceptibility.

18. The method of claim 16, wherein the individual phage-host lytic susceptibility matrix comprises values of observed lytic activity, binary values of interaction or non-interaction, or a combination thereof.

19. The method of claim 18, wherein the binary values comprise values of $\{0,1\}$.

20. The method of claim 1, wherein (a) further comprises using Bayesian Optimization, Bayesian Regression, Linear Programming, Association Rules, Reinforcement Learning, or a combination thereof.

21. The method of claim 1, wherein the set of constraints comprise maximum phage number, minimum phage number, coverage, and genetic diversity.

22. The method of claim 1, wherein predicting the lytic susceptibility comprises using a Random Forest, Logistic Regression, Support Vector Machines, XGBoost, Logistic Regression, Deep Neural Networks (DNN), Recurrent Neural Networks (RNN), Bayesian Neural Networks, Bayesian Regression, Reinforcement Learning, Graph Neural Networks, or a combination thereof.

23. The method of claim 1, further comprising using base constraints to group phages into random subsets of representative isolates.

24. The method of claim 23, wherein the phages are grouped based on a criterion that each host must have lytic susceptibility to at least one phage in the phage cocktail.

25. The method of claim 23, wherein the phages are grouped based at least in part on a degree of genetic similarity.

26. The method of claim 25, wherein the degree of genetic similarity is determined based on a distance between DNA sequences of the phages.

27. The method of claim 23, wherein the base constraints comprise a constraint that the phages are genetically diverse from each another.

28. The method of claim 23, wherein the base constraints comprise a constraint that the number of phages in the cocktail is at least two phages while maximizing the host range of the cocktail.

* * * * *